(12) United States Patent
Lauer (10) Patent No.: US 6,488,026 B2
(45) Date of Patent: Dec. 3, 2002

(54) UNIVERSAL OXYGEN CONNECTOR

(76) Inventor: Mark A. Lauer, 1693 Juno Ave., St. Paul, MN (US) 55116

( * ) Notice: Subject to any disclaimer, the term of this patent is extended or adjusted under 35 U.S.C. 154(b) by 0 days.

(21) Appl. No.: 09/755,261

(22) Filed: Jan. 5, 2001

(65) Prior Publication Data

US 2002/0124845 A1 Sep. 12, 2002

(51) Int. Cl.$^7$ ............................................. A62B 9/04
(52) U.S. Cl. ............................. 128/202.27; 128/912
(58) Field of Search ............................ 285/138, 196, 285/238, 239; 128/202.27, 912

(56) References Cited

U.S. PATENT DOCUMENTS

| | | | | |
|---|---|---|---|---|
| 2,112,290 A | * | 3/1938 | Holland | 285/238 |
| 2,655,918 A | * | 10/1953 | Jones | 285/238 |
| 2,874,981 A | * | 2/1959 | Brady | 285/238 |
| 3,791,406 A | * | 2/1974 | Philipps | 285/239 |
| 3,960,142 A | * | 6/1976 | Elliott et al. | 128/205.11 |
| 4,453,747 A | * | 6/1984 | Bimba | 285/238 |
| 5,690,097 A | * | 11/1997 | Howard et al. | 128/205.11 |
| 6,227,579 B1 | * | 5/2001 | Humphreys | 285/239 |

* cited by examiner

Primary Examiner—Aaron J. Lewis
(74) Attorney, Agent, or Firm—Hugh D. Jaeger (57) ABSTRACT

A universal oxygen connector for connecting an oxygen supply tubing or an oxygen supply hose between and an oxygen supply appliance and an oxygen mask or a nasal oxygen dispenser. Multiple and aligned and spaced hose or tubing connection bodies on a single universal oxygen connector accepts oxygen supply tubing or an oxygen supply hose for use as required.

3 Claims, 8 Drawing Sheets

UNIVERSAL OXYGEN CONNECTOR

CROSS REFERENCES TO CO-PENDING APPLICATIONS

None.

BACKGROUND OF THE INVENTION

1. Field of the Invention

The present invention is for a medical device and, more particularly, is for an oxygen connector that can be incorporated for use with an oxygen tubing or hose, each having a different diameter.

2. Description of the Prior Art

Prior art oxygen connectors are fashioned to connect at their proximal end to supply oxygen from an oxygen tank flow meter or to supply oxygen from a flow meter which is connected to a wall-mounted oxygen outlet, each method utilizing common sized threaded surfaces for connection. However, connection of a large oxygen supply hose or a small oxygen supply tubing at the connector distal end is not afforded such convenient commonality and as such various sized connectors must be utilized depending on the size of oxygen conveyance desired, be it a large oxygen supply hose or a small oxygen supply tubing. The practitioner first must determine whether a large oxygen supply hose or a small oxygen supply tubing must be used, and then must select and subsequently install and utilize the properly dimensioned oxygen connector. Often after surgery oxygen requirements are needed, thereby requiring an oxygen supply hose or tubing. Such determination of and installation of the properly dimensioned oxygen hose or tubing requires extra time, effort, inconvenience and cost. Clearly, what is required is an oxygen connector which accommodates either an oxygen hose or tubing and which reduces practitioner workload and overcomes the problems associated with prior art devices.

SUMMARY OF THE INVENTION

The general purpose of the present invention is to provide a universal oxygen connector which can be incorporated for use with either a small oxygen supply tubing or a large oxygen supply hose. The universal connector attaches at one end to an oxygen supply appliance, such as an oxygen tank flow meter, or to a wall-mounted flow meter. Oxygen supply tubing or an oxygen supply hose can be attached to the remaining end of the universal connector, and the tubing or hose can lead to and supply oxygen to a nasal oxygen dispenser or an oxygen mask, as required. The universal oxygen connector includes concentrically aligned, but longitudinally spaced, connection bodies of at least two different radii for connection, one at a time, to an oxygen supply hose or to an oxygen supply tubing. The smaller tubing connection body accepts and frictionally engages one end of an oxygen supply tubing which communicates through a centrally located lumen which is partially located within the tubing connection body and partially located within a large hose connection body. The lumen also communicates with a sealing gland located at the proximal end of a main body where the sealing gland mates with an oxygen supply appliance.

The larger hose connection body accepts and frictionally engages one end of an oxygen supply hose which also encompasses and surrounds the tubing connection body. The acceptance of the oxygen supply hose over and about the hose connection body provides for communication of the oxygen supply hose with the tubing connection body generally, and specifically with the lumen extending partially through the tubing connection body and extending partially within the large hose connection body, whereby communication through the plastic sealing gland to the oxygen supply appliance occurs.

According to one or more embodiments of the present invention, there is provided a universal oxygen connector having a cylindrically shaped main body the proximal end of which is threaded for connection to an oxygen supply appliance, a hose connection body of relatively large radius having an annular hose connection surface each being contiguous with and extending distally from the region of the main body, a tubing connection body having an annular tubing connection surface of relatively small radius, each being continuous with and extending distally from the region of the hose connection body, a barb located at the end of the tubing connection body, a plastic sealing gland centrally located at the proximal end of the main body, and, a lumen extending through the tubing connection body, the hose connection body and partially into the main body to communicate with the plastic sealing gland and with an oxygen supply appliance.

One significant aspect and feature of the present invention is a universal oxygen connector.

Another significant aspect and feature of the present invention is a universal oxygen connector which includes a hose connection body.

Still another significant aspect and feature of the present invention is a universal oxygen connector which includes a tubing connection body.

Yet another significant aspect and feature of the present invention is a universal oxygen connector which accepts at least two differently sized oxygen transfer means.

A further significant aspect and feature of the present invention is a universal oxygen connector which reduces changeout of connectors for oxygen transfer means of different size.

Having thus described embodiments of the present invention, it is the principal object of the present invention to provide a universal oxygen connector.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
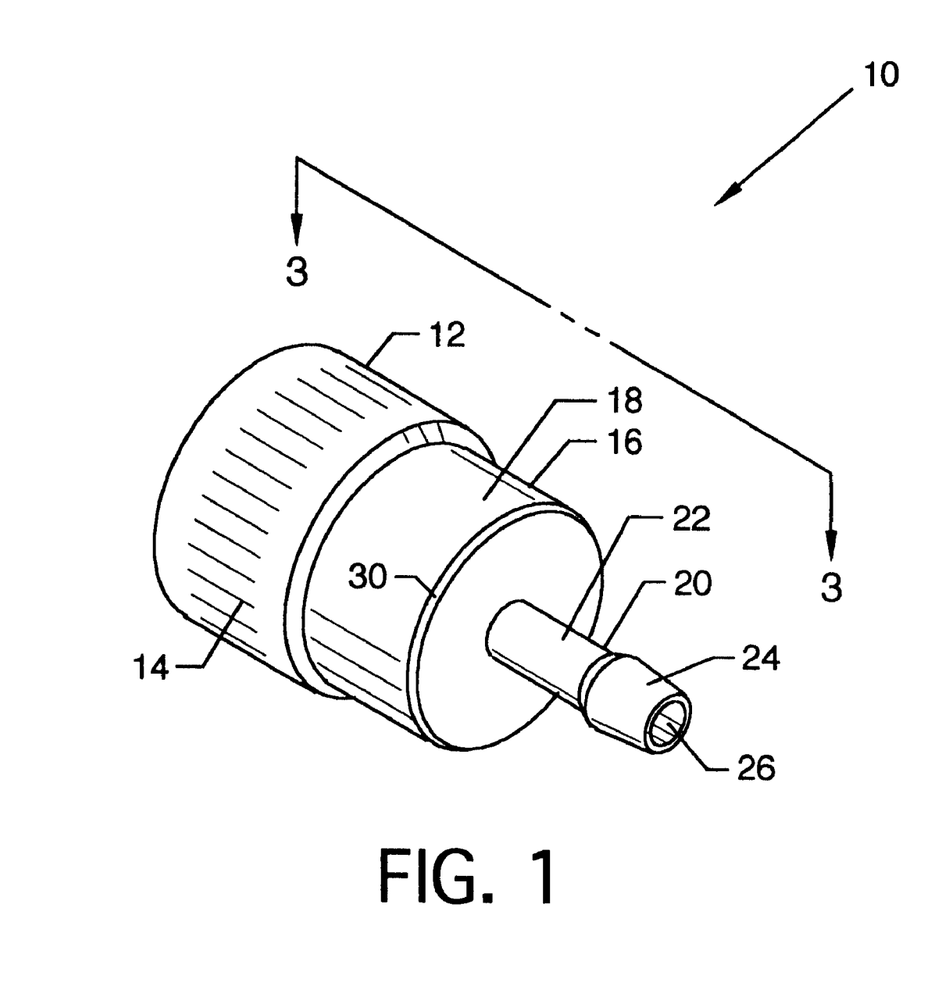
FIG. 1 illustrates an isometric view of the distal region of a universal oxygen connector, the present invention.

FIG. 1 illustrates an isometric view of the distal region of a universal oxygen connector 10, the present invention. The universal oxygen connector 10 is fashioned of a suitable metal substantially in a one-piece form with the exception of a plastic sealing gland shown later in detail. Visible components and features of the universal oxygen connector 10 include a cylindrical main body 12 having a textured gripping surface 14, a hose connection body 16 having an annular hose connection surface 18, each extending distally from the main body 12, a tubing connection body 20 having an annular tubing connection surface 22, each extending distally from the hose connection body 16, a barb 24 at the distal end of the tubing connection body 20, and a lumen 26 which in part extends through the tubing connection body 20 and in part extends through the hose connection body 16 to communicate with a plastic sealing gland 28 shown in FIGS. 2, 3 and 4. A chamfered surface 30 is included at the distal region of the hose connection body 16 to facilitate accommodation of an oxygen supply hose.

Figure 2:
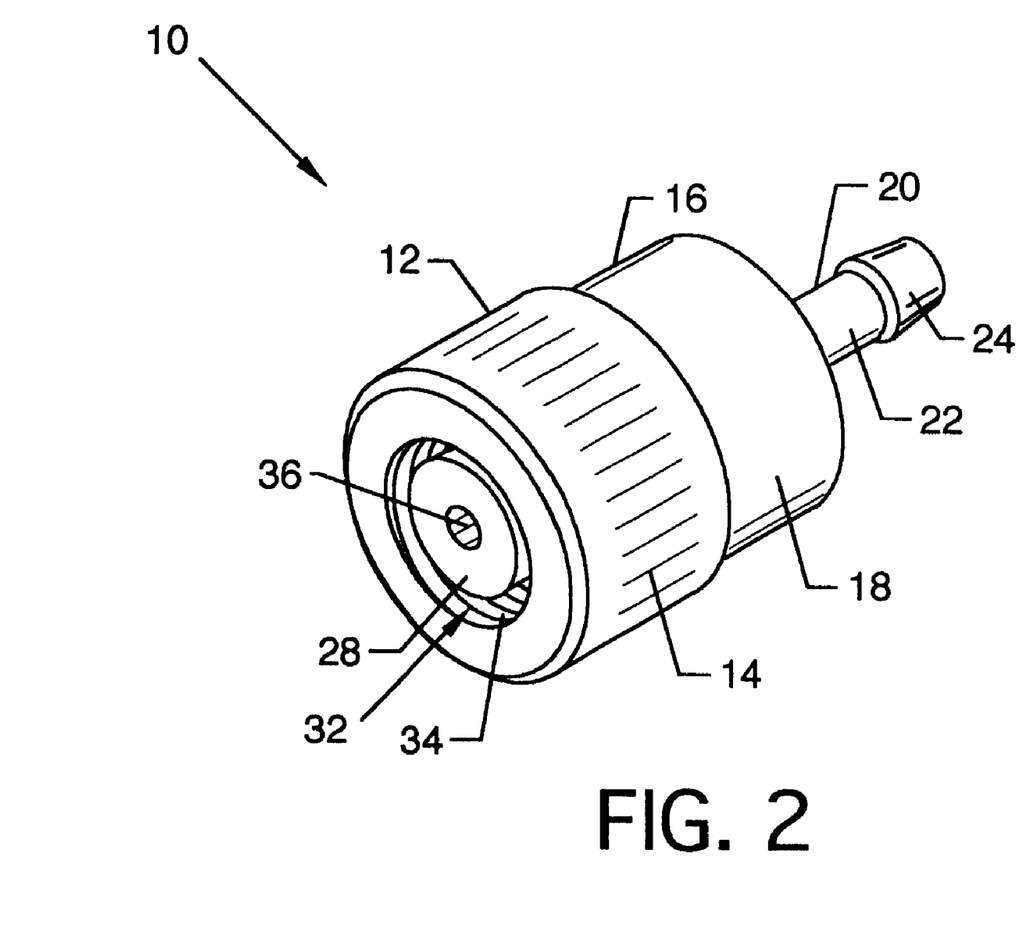
FIG. 2 illustrates an isometric view of the proximal region of the universal oxygen connector.

FIG. 2 illustrates an isometric view of the proximal region of the universal oxygen connector 10. Additional visible components and features of the universal oxygen connector 10 include a chamber 32 interior to the main body 12 having a threaded surface 34, and a plastic sealing gland 28 residing in the chamber 32. The plastic sealing gland 28 includes a lumen 36 which aligns to and communicates with lumen 26 previously described in connection with FIG. 1.

Figure 3:
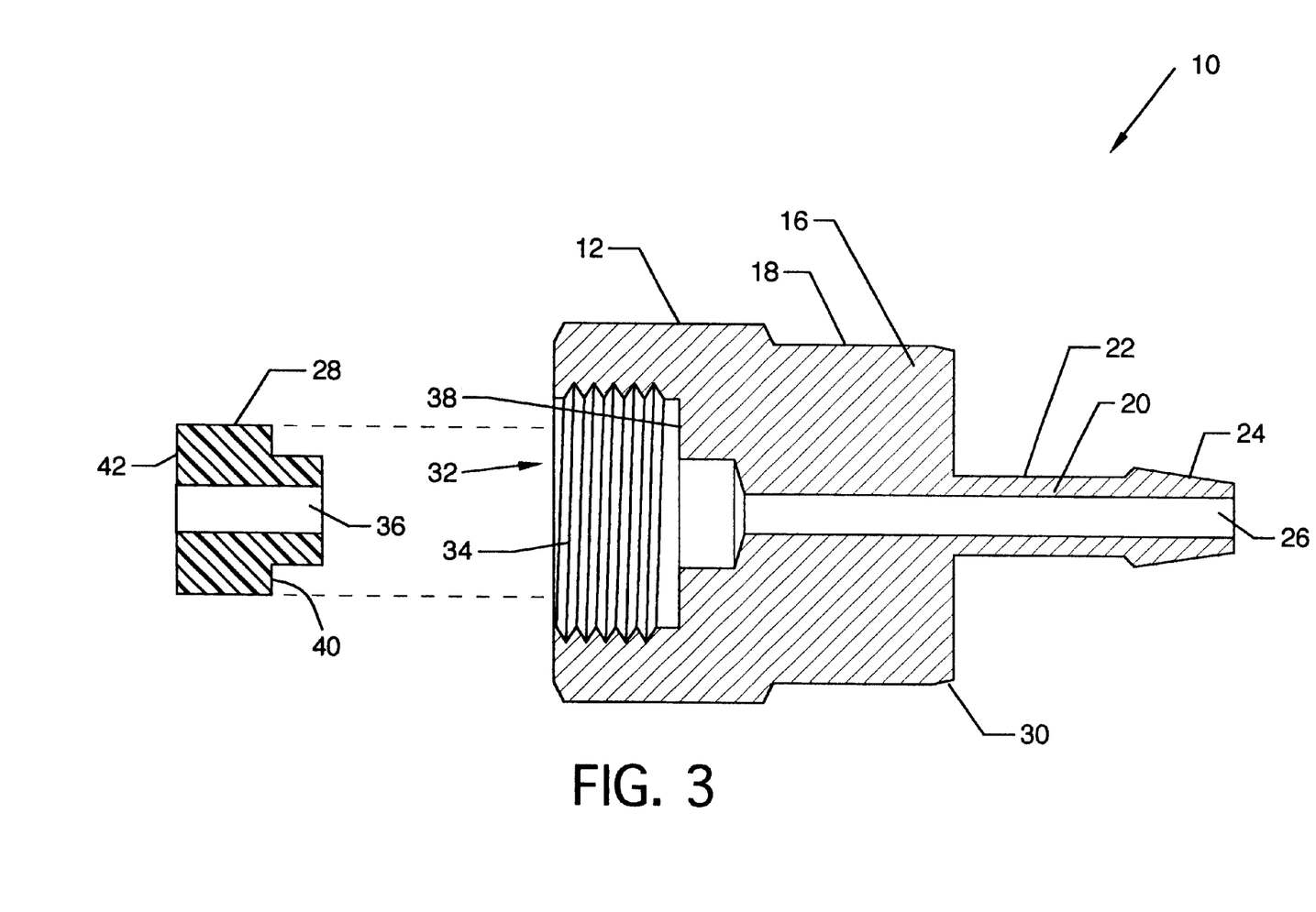
FIG. 3 illustrates an exploded cross-section view of the universal oxygen connector along line 3—3 of FIG. 1.

FIG. 3 illustrates an exploded cross-section view of the universal oxygen connector 10 along line 3—3 of FIG. 1. Illustrated in particular is the lumen 26 extending in part through the tubing connection body 20 and in part through the hose connection body 16 and partially into the main body 12. The lumen 26 assumes a larger cross section at the main body 12 and aligns to and with the chamber 32. Chamber 32 includes an interior annular mating surface 38 adjoining the lumen 26. The plastic sealing gland 28 includes an annular mating surface 40 corresponding to the interior annular mating surface 38 adjoining the lumen 26. The lumen 36 of the plastic sealing gland 28 is sealed to the lumen 26 by the mating of the annular mating surface 40 to the annular mating surface 38. An annular mating surface 42 at the proximal end of the plastic sealing gland 28 is provided for mating to an appropriate oxygen supply appliance.

Figure 4:
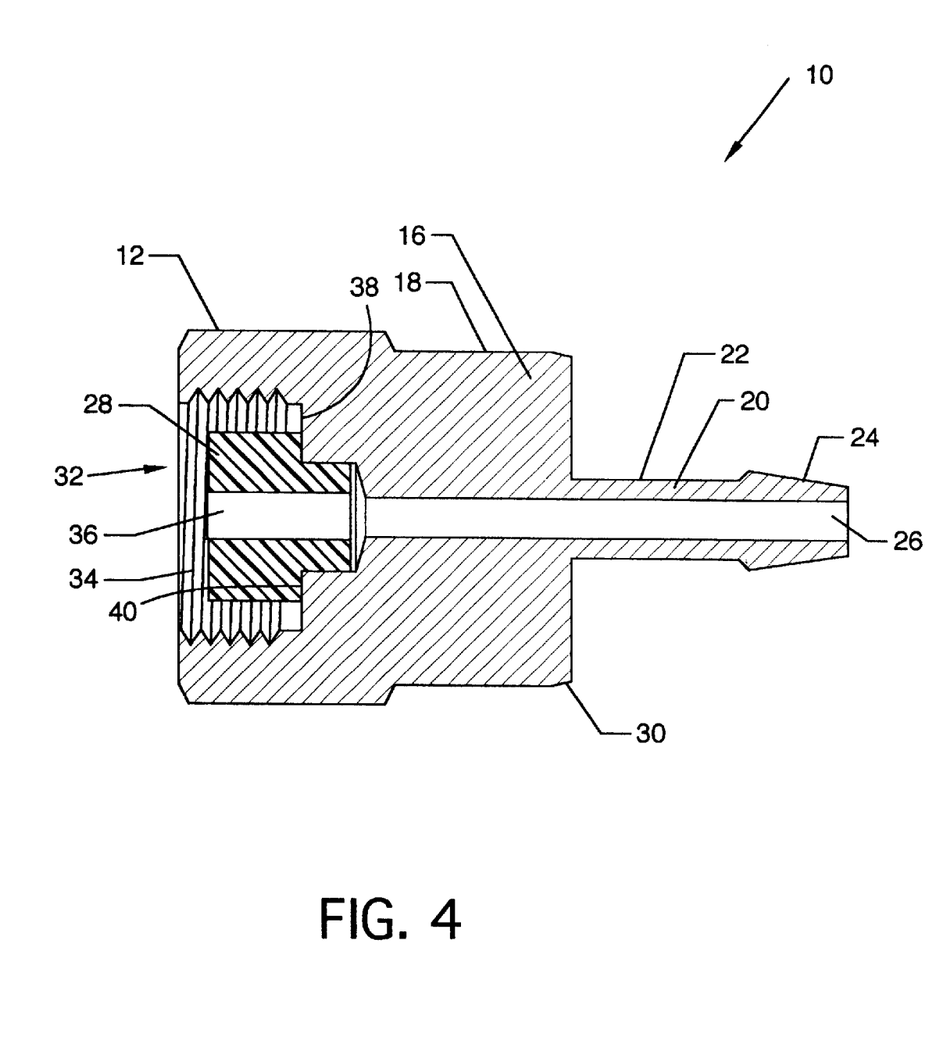
FIG. 4 illustrates an assembled cross-section view of the components of FIG. 3.

FIG. 4 illustrates an assembled cross-section view of the components of FIG. 3. Illustrated in particular is the lumen 26 in communication with lumen 36 of the plastic sealing gland 28. As an alternative to the previously described construction, the universal oxygen connector 10 of the instant invention can be fashioned entirely of plastic and in one piece, thereby eliminating the need for separate machining and tooling for fabrication of a universal oxygen connector comprised of two separate parts.

MODE OF OPERATION

Figure 5:
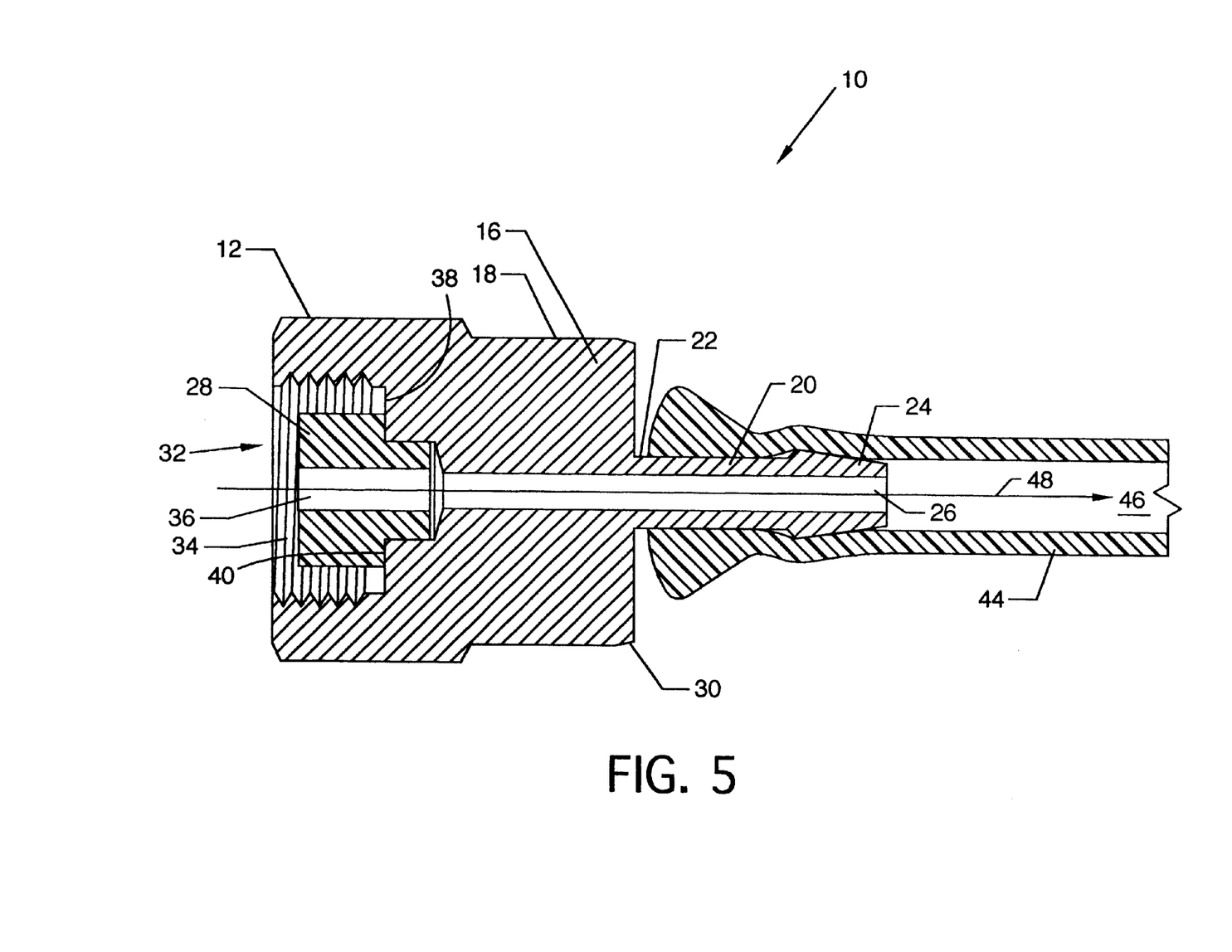
FIG. 5 illustrates the mode of operation of the universal oxygen connector with an oxygen supply tubing.

FIG. 5 illustrates the mode of operation of the universal oxygen connector 10 with an oxygen supply tubing 44. Illustrated in particular is the frictional engagement of the oxygen supply tubing 44 with the annular tubing connection surface 22 and barb 24 of the tubing connection body 20 to provide communication of the lumen 46 of the oxygen supply tubing 44 with lumens 26 and 36 of the universal oxygen connector 10. Oxygen from an oxygen supply appliance flows through lumen 36, through lumen 26, and thence through the lumen 46 of the oxygen supply tubing 44, as indicated by arrow 48, to be used by an oxygen mask or nasal oxygen dispenser.

Figure 6:
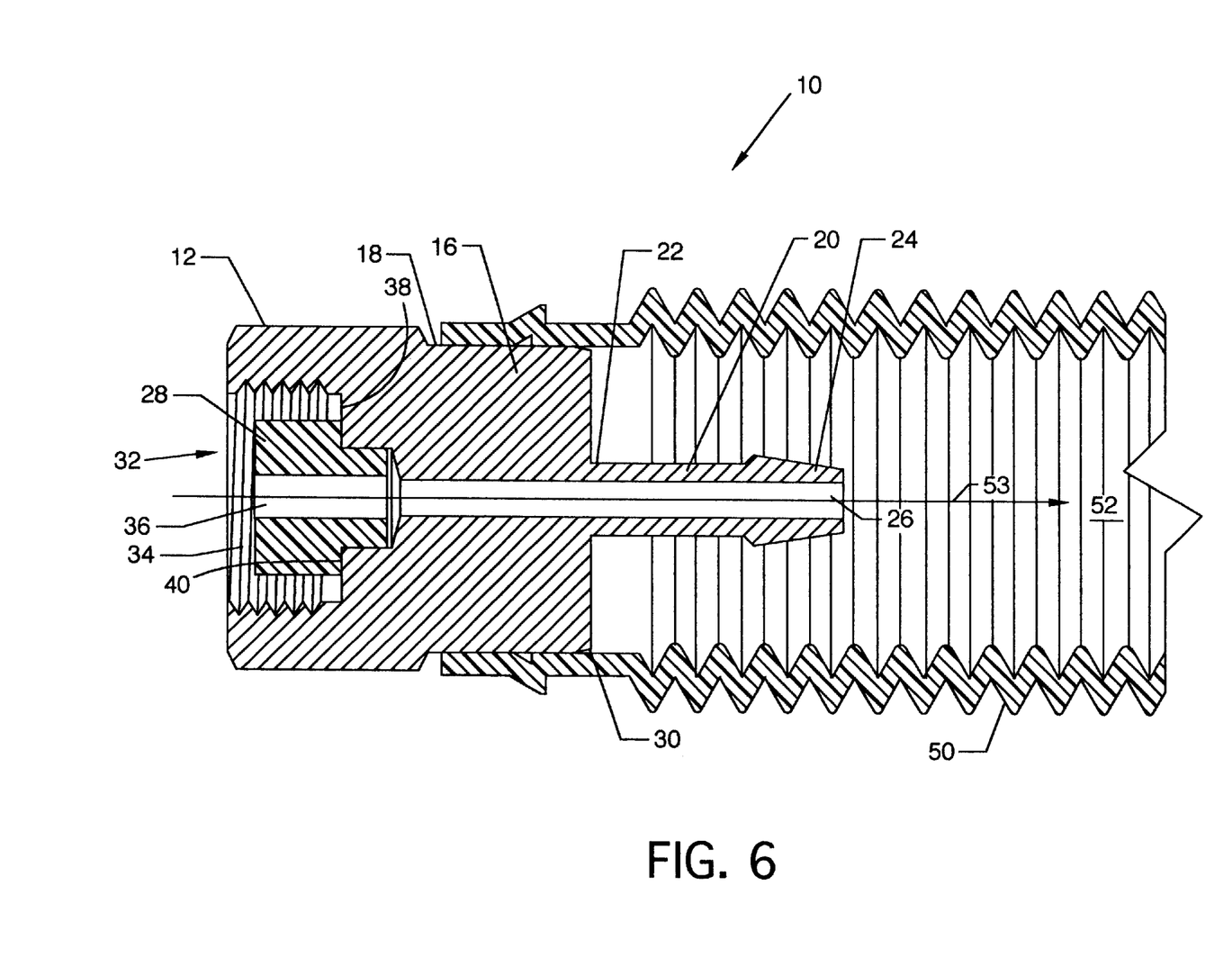
FIG. 6 illustrates the mode of operation of the universal oxygen connector with an oxygen supply hose.

FIG. 6 illustrates the mode of operation of the universal oxygen connector 10 with an oxygen supply hose 50. Illustrated in particular is the frictional engagement of the oxygen supply hose 50 with the annular hose connection surface 18 of the hose connection body 16 to provide communication of the lumen 52 of the oxygen supply hose 50 with lumens 26 and 36 of the universal oxygen connector 10. Oxygen from an oxygen supply appliance flows through lumen 36, through lumen 26, and thence through the lumen 52 of the oxygen supply hose 50, as indicated by arrow 53, to be used by an oxygen mask.

Figure 7:
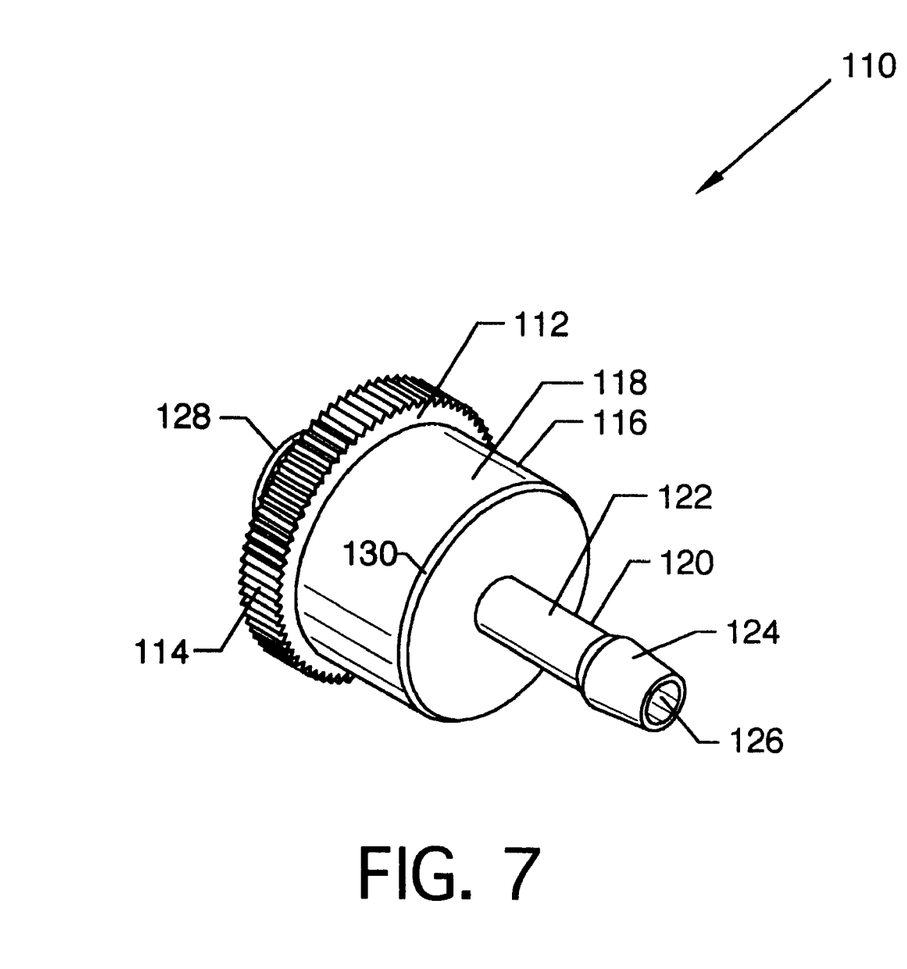
FIG. 7, an alternative embodiment, illustrates an isometric view of the distal region of a universal oxygen connector; and, FIG. 8 illustrates an isometric view of the proximal region of the universal oxygen connector of FIG. 7.

FIG. 7, an alternative embodiment, illustrates an isometric view of the distal region of a universal oxygen connector 110 for use with an oxygen tank flow meter, an oxygen supply appliance. The universal oxygen connector 110 is fashioned of a suitable metal or alternatively of a suitable plastic, substantially in a one-piece form. Visible components and features of the universal oxygen connector 110 include a cylindrical and shortened main body 112 having a grooved, knurled or otherwise textured gripping surface 114, a hose connection body 116 having an annular hose connection surface 118, each extending distally from the main body 112, a tubing connection body 120 having an annular tubing connection surface 122, each extending distally from the hose connection body 116, a barb 124 at the distal end of the tubing connection body 120, and a lumen 126 which in part extends through the small tubing connection body 120, in part extends through the hose connection body 116, in part extends through the main body 112, and in part extends through a contiguous threaded connection port 128 extending proximally from the main body 112 to communicate with an oxygen supply appliance. A chamfered surface 130 is included at the distal end of the hose connection body 116 to facilitate accommodation of an oxygen supply hose.

Figure 8:
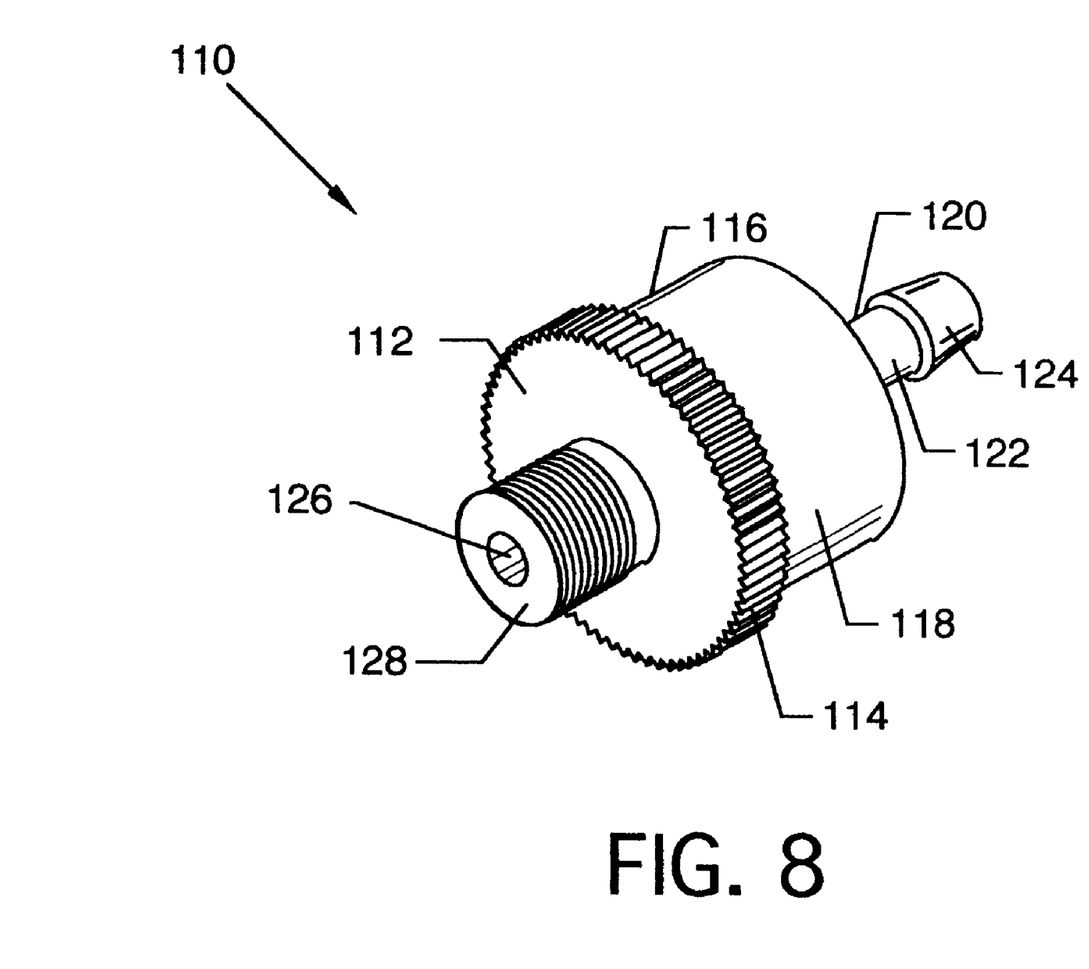

FIG. 8 illustrates an isometric view of the proximal region of the universal oxygen connector 110. Additional visible components and features of the universal oxygen connector 110 include the threaded connection port 128 which threadingly engages a suitable oxygen tank flow meter port. The universal oxygen connector 110 accepts oxygen supply tubing and hoses as previously described for the universal oxygen connector 10. Frictional engagement of the oxygen supply tubing 44 of FIG. 5 with the annular tubing connection surface 122 and barb 124 of the tubing connection body 120 is provided for communication. of the lumen 46 of the oxygen supply tubing 44 with lumen 126 of the universal oxygen connector 110. Frictional engagement of the oxygen supply hose 50 of FIG. 6 with the annular hose connection surface 118 of the hose connection body 116 is provided for communication of the lumen 52 of the oxygen supply hose 50 with lumen 126 of the universal oxygen connector 110.

Various modifications can be made to the present invention without departing from the apparent scope hereof.

UNIVERSAL OXYGEN CONNECTOR

PARTS LIST 10 universal oxygen connector
12 main body
14 gripping surface
16 hose connection body 18 annular hose connection surface
20 tubing connection body
22 annular tubing connection surface
24 barb
26 lumen
28 plastic sealing gland
30 chamfered surface
32 chamber
34 threaded surface
36 lumen
38 annular mating surface
40 annular mating surface
42 annular mating surface
44 oxygen supply tubing
46 lumen (of oxygen supply tube)
48 arrow
50 oxygen supply hose
52 lumen (of oxygen supply hose)
53 arrow
110 universal oxygen connector
112 main body
114 knurled, grooved, or otherwise textured gripping surface
116 hose connection body
118 annular hose connection surface
120 tubing connection body
122 annular tubing connection furface
124 barb
126 lumen
128 threaded connection port
130 chamfered surface What it is claimed:

1. A universal oxygen connector comprising:
  a. cylindrically shaped main body, the main body having a proximal end and a distal end and textured gripping surface between the proximal end and the distal end of the main body,
  b. a hose connection body, the hose connection body having a proximal end, a distal end and a first radius and having an annular hose connection surface each being continuous with and extending distally from the distal end of the main body, the annular hose connection surface further including a chamfered surface at the distal and of the hose connection body to facilitate hose accommodation upon the annular hose connection surface;
  c. a tubing connector body, the tubing connector body having a second radius, smaller than the first radius and having an annular tubing connection surface, each being continuous with and extending distally from the region of the hose connection body;
  d. a barb located at the end of the tubing connection body;
  e. a threaded connection port extending proximally from the proximal end of the main body, for connection to an oxygen supply appliance; and,
  f. a lumen extending through the tubing connection body, the hose connection body, the main body, and the threaded connection port to communicate with the oxygen supply appliance and allow oxygen to be supplied to either a hose connected to the hose connection body or a tubing connected to the tubing connector body.

2. The universal oxygen connector of claim 1, wherein the connector is formed of metal.

3. The universal oxygen connector of claim 1, wherein the connector is formed of plastic.

* * * * *